(12) United States Patent
Char et al.

(10) Patent No.: US 9,561,293 B2
(45) Date of Patent: Feb. 7, 2017

(54) PREPARATION METHOD OF ORGANIC MICROBUBBLE COMPLEX PARTICLE, ORGANIC MICROBUBBLE COMPLEX PARTICLE, AND ULTRASOUND CONTRAST AGENT

(71) Applicant: SNU R&DB FOUNDATION, Seoul (KR)

(72) Inventors: Kookheon Char, Seoul (KR); Saibom Park, Seoul (KR)

(73) Assignee: SNU R&DB FOUNDATION, Seoul (KR)

( * ) Notice: Subject to any disclaimer, the term of this patent is extended or adjusted under 35 U.S.C. 154(b) by 98 days.

(21) Appl. No.: 14/200,189

(22) Filed: Mar. 7, 2014

(65) Prior Publication Data

US 2015/0125399 A1 May 7, 2015

(30) Foreign Application Priority Data

Nov. 6, 2013 (KR) .................. 10-2013-0134213

(51) Int. Cl.
*A61B 8/00* (2006.01)
*A61K 49/22* (2006.01)

(52) U.S. Cl.
CPC ............ *A61K 49/223* (2013.01); *A61K 49/22* (2013.01)

(58) Field of Classification Search
None
See application file for complete search history.

(56) References Cited

U.S. PATENT DOCUMENTS

2012/0237450 A1* 9/2012 Wheatley ............ A61K 49/223
424/9.5
2014/0165545 A1* 6/2014 Pinkerton ............... B32B 9/007
60/325

FOREIGN PATENT DOCUMENTS

| KR | 10-2005-0096959 | 10/2005 | |
| NL | WO 2011144321 A1 * | 11/2011 | ............ C08J 3/215 |
| WO | 2004-006964 | 1/2004 | |

OTHER PUBLICATIONS

Xu et al. (Appl. Phys. Lett. 2006, 88, 133506-1 to 133506-3).*
Arakawa et al. (Sensors and Actuators A 2008, 143, 58-63).*
Sametband et al. (New J. Chem. 2012, 36, 36-39).*

* cited by examiner

*Primary Examiner* — Michael G Hartley
*Assistant Examiner* — Melissa Perreira
(74) *Attorney, Agent, or Firm* — Lex IP Meister, PLLC

(57) ABSTRACT

This disclosure relates to a method for preparing organic microbubble complex particles including sonicating an aqueous solution including a graphene compound and an amphiphilic material in the presence of a gas, a method for preparing organic microbubble complex particles including injecting an aqueous solution including a graphene compound and an amphiphilic material into a microchannel, and an organic microbubble complex particle including a core part including at least one gas selected from the group consisting of an inert gas and carbon dioxide, and a shell layer including a graphene compound and an amphiphilic material, and an ultrasound contrast agent including the organic microbubble complex particles.

7 Claims, 7 Drawing Sheets

Figure 2
(a)
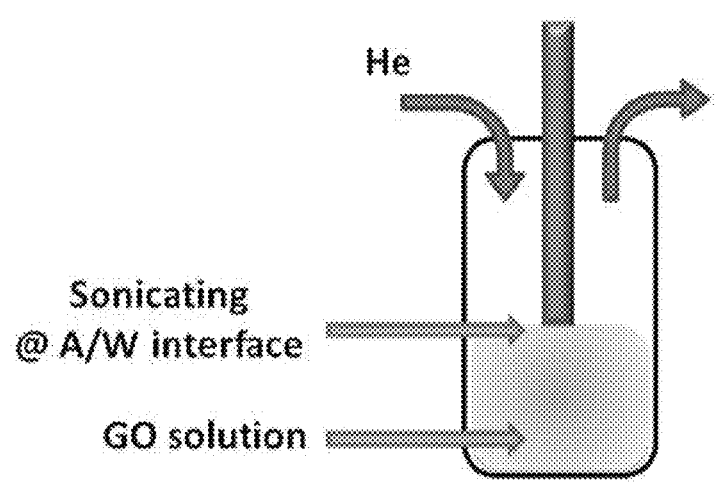
(b)
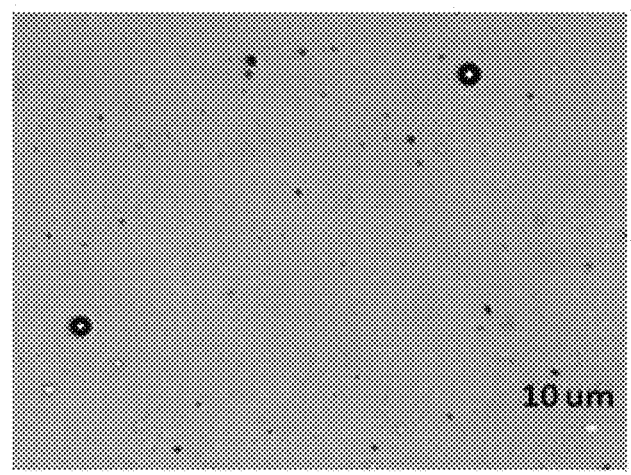

Figure 3
(a)
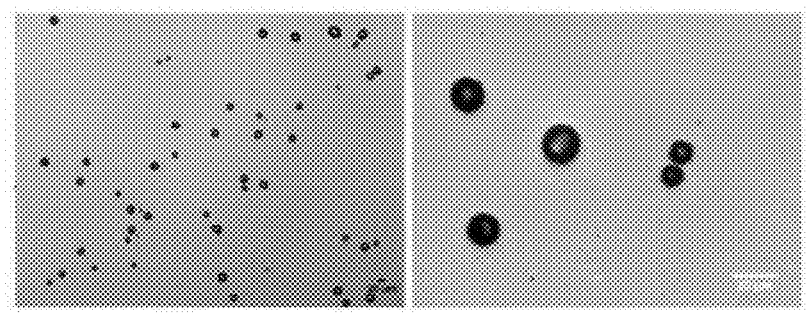
(b)
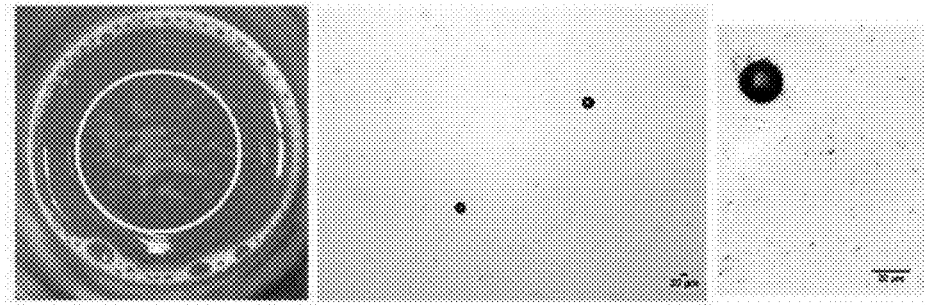

US 9,561,293 B2

PREPARATION METHOD OF ORGANIC MICROBUBBLE COMPLEX PARTICLE, ORGANIC MICROBUBBLE COMPLEX PARTICLE, AND ULTRASOUND CONTRAST AGENT

CROSS-REFERENCE TO RELATED APPLICATION

This application claims priority to and the benefit of Korean Patent Application No. 10-2013-0134213 filed in the Korean Intellectual Property Office on Nov. 6, 2013, the entire contents of which are incorporated herein by reference.

BACKGROUND OF THE INVENTION (a) Field of the Invention

The present invention relates to a method for preparing organic microbubble complex particles, organic microbubble complex particles, and a contrast agent, and more particularly, to organic microbubble complex particles that have high uniformity of particle size and excellent long term shape stability and storage stability, a preparation method thereof, and a contrast agent having an excellent enhancement effect, stability, and excellent reproducibility of ultrasound contrast.

(b) Description of the Related Art

A bubble is a spherical body consisting of a gas suspending in a liquid. A bubble of a stable structure may be applied in the fields of acoustic bandgap materials and functional light-weight materials, as well as in food and cosmetic industries.

Further, bubbles may be used for biomedical applications such as contrast-enhanced ultrasonography, drug or gene delivery by ultrasound, and the like, and bubbles of a micrometer size that have a high compression rate and scattering elasticity compared to an aqueous medium are also used as an ultrasound contrast agent.

Ultrasound contrast agents have been in development since Gramiak and Shah discovered that an ultrasound signal is enhanced after injecting microbubbles into a blood vessel in 1968, and currently, myocardial perfusion is evaluated by administering microbubbles that can enhance reflection of ultrasound and indirectly measuring ultrasound reflectivity of the myocardium.

That is, if a contrast agent is administered and then ultrasound is applied, the ultrasound is reflected by microbubbles in the contrast agent to more clearly show an image of the myocardium.

Commonly, in ultrasound contrast agents, bubbles formed by injecting a gas such as nitrogen and the like in an aqueous medium have been used, but according to the previous method, it was difficult to prepare bubbles having a uniform size and required properties, and the prepared bubbles had a limitation in that they could not maintain the shape or exist in an aqueous medium for a long time required for diagnosis.

Recently, a method of preparing bubbles by adding a surfactant or other surface stabilizing materials to an aqueous medium and injecting gas has been known. However, although the prepared bubbles may secure structural stability to a specific degree, they have limitations in that it is difficult to mass-produce them with a constant size, they may not have sufficient performance as ultrasound contrast agents such as a high enhancement effect or excellent reproducibility of ultrasound contrast, and it is not easy to keep them for a long time after preparation.

SUMMARY OF THE INVENTION

It is an object of the present invention to provide organic microbubble complex particles that have high uniformity of particle sizes and excellent long term shape stability and storage stability.

It is another object of the present invention to provide a method for preparing the organic microbubble complex particles.

It is still another object of the present invention to provide a contrast agent that has a high enhancement effect, stability, and excellent reproducibility of ultrasound contrast.

There is provided a method for preparing organic microbubble complex particles, including sonicating an aqueous solution including a graphene compound and an amphiphilic material, in the presence of a gas including at least one selected from the group consisting of an inert gas and carbon dioxide.

There is also provided a method for preparing organic microbubble complex particles, including injecting an aqueous solution including a graphene compound and an amphiphilic material, and a gas, into a microchannel.

There is also provided an organic microbubble complex particle including a core part including at least one gas selected from the group consisting of an inert gas and carbon dioxide, and a shell layer including a graphene compound and an amphiphilic material.

BRIEF DESCRIPTION OF THE DRAWINGS

FIG. 2 shows (a) one example of the preparation method of organic microbubble complex particles using ultrasonication in Comparative Example 2, and (b) an optical microscopic photograph of the organic microbubble complex particles obtained in Comparative Example 2.

FIG. 3 shows (a) optical microscopic photographs of the organic microbubble complex particles prepared in Example 1, and (b) optical microscopic photographs of the microbubble complex particles after 3 days had passed from the preparation.

DETAILED DESCRIPTION OF THE EMBODIMENTS

Figure 1:
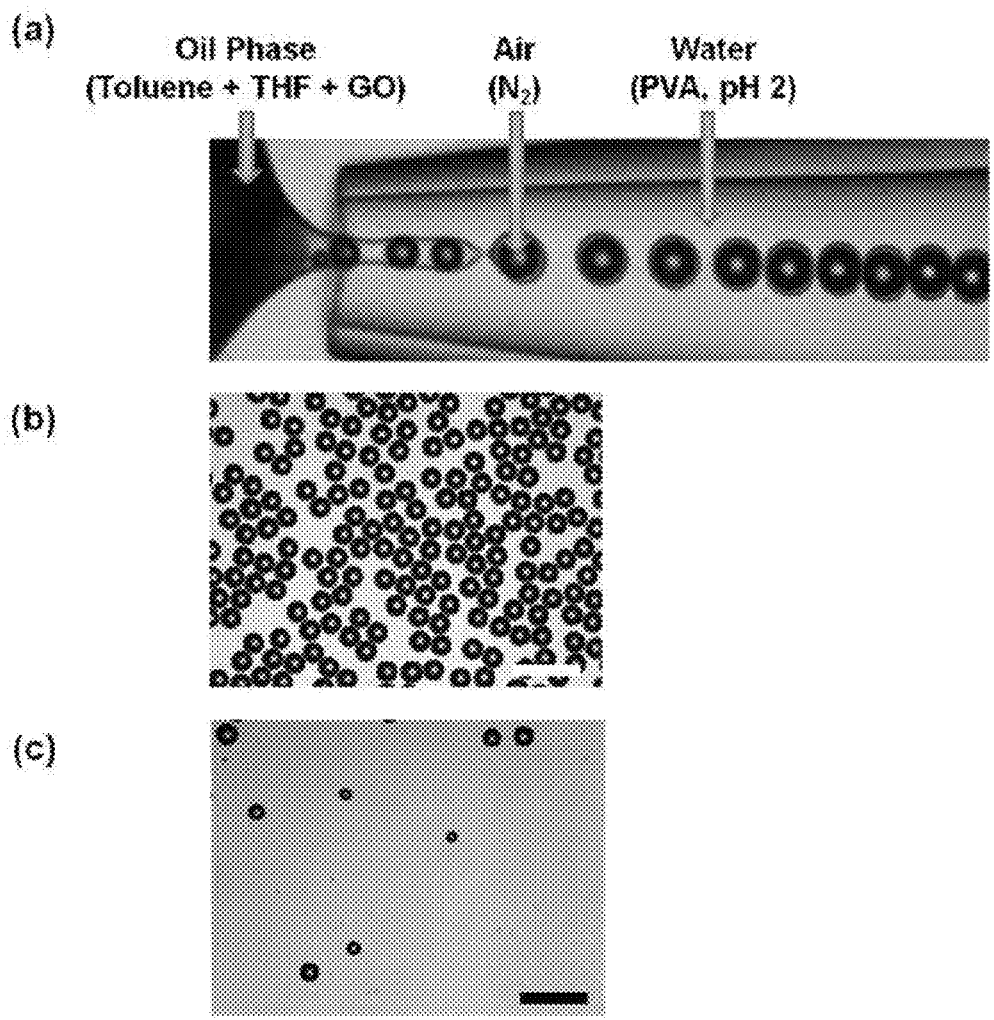
FIG. 1 shows (a) one example of the preparation method of the organic microbubble complex particles of Comparative Example 1, (b) an optical microscopic photograph of the organic microbubble complex particles when the preparation is completed, and (c) an optical microscopic photograph of the organic microbubble complex particles after 10 minutes had passed from the preparation.

Hereinafter, a method for preparing organic microbubble complex particles, organic microbubble complex particles, and an ultrasound contrast agent according to specific embodiments of the invention will be explained in detail.

As used herein, an "organic microbubble complex particle" refers to a particle including a bubble of a micrometer (μm) size and organic ingredients, and for example, it may be a microparticle including a core part of a micrometer (μm) size including gas, and a shell layer including organic ingredients, which surrounds the core part.

According to one embodiment of the invention, a method for preparing organic microbubble complex particles is provided, including sonicating an aqueous solution including a graphene compound and an amphiphilic material, in the presence of gas including at least one selected from the group consisting of an inert gas and carbon dioxide.

The inventors confirmed through experimentation that organic microbubble complex particles may be formed by sonication of an aqueous solution including a graphene compound and an amphiphilic material in the presence of an inert gas and/or carbon dioxide, and that the prepared organic microbubble complex particles have high structural stability, may continue to exist in an aqueous solution for a long time, have little difference in particle size or particle diameter, and when used as an ultrasound contrast agent, may achieve a high enhancement effect and excellent reproducibility of ultrasound contrast, and completed the invention.

The graphene compound, although it is organic material, may deliver drugs through a photothermal effect at a near infrared region like inorganic metal particles such as gold or silver, and the like, and thus the organic microbubble complex particles prepared by the above method may be applied for a system simultaneously conducting diagnosis and treatment.

Particularly, by using the amphiphilic material, the prepared organic microbubble complex particles may continue to exist in an aqueous solution for a long time, and by applying the sonication, the prepared organic microbubble complex particles have a specific structure as described below, and thus a more stable structure and a narrow particle size distribution may be achieved.

The organic microbubble complex particle according to one embodiment includes two or more organic microbubble complex particle groups as well as one organic microbubble complex particle.

The prepared organic microbubble complex particle may have a maximum diameter of 1 μm to 500 μm, or 5 μm to 200 μ2, and the maximum diameter may be distributed within a range of 50% to 150%, or 70% to 130%, based on the average maximum diameter.

Specifically, the longest diameters of two or more organic microbubble complex particles included in the organic microbubble complex particle of one embodiment may be 50% to 150%, or 70% to 130% compared to the mean of the longest diameters of the two or more organic microbubble complex particles.

By conducting sonication of an aqueous solution including a graphene compound and an amphiphilic material in the presence of a gas including at least one selected from the group consisting of an inert gas and carbon dioxide, the organic microbubble complex particle may be prepared.

The prepared organic microbubble complex particle may include a core part including at least one gas selected from the group consisting of an inert gas and carbon dioxide, and a shell layer including a graphene compound and an amphiphilic material.

The shell layer may have a thickness of 0.01 μm to 100 μm, or 0.1 μm to 50 μm.

Further, the shell layer may be a porous layer including micropores having a maximum diameter of 0.001 μm to 1 μm.

The organic microbubble complex particle prepared by the above method, when redispersed in an aqueous solution after drying, may be immediately reconverted to a state before drying or to a bubble state due to the firm structure of the shell layer including a graphene compound and an amphiphilic material, and thus it may facilitate a commercial distribution process, and it may have various advantages in application as a contrast agent.

Further, the prepared organic microbubble complex particle may be used as an ultrasound contrast agent due to the bubble property, and simultaneously, it may irradiate light after ultrasound diagnosis due to the photothermal effect of the graphene compound included in the shell layer and deliver drugs to a desired location, thus enabling a theragnosis (therapy+diagnosis) system capable of simultaneously conducting diagnosis and treatment.

Meanwhile, the sonication of an aqueous solution including a graphene compound and an amphiphilic material may be conducted in the presence of a gas including at least one selected from the group consisting of an inert gas and carbon dioxide.

Specific examples of the inert gas may include helium, neon, argon, krypton, xenon, radon, and nitrogen, and the sonication of an aqueous solution including a graphene compound and an amphiphilic material may preferably be conducted in the presence of nitrogen, helium, carbon dioxide, or a mixture thereof.

The sonication of an aqueous solution including a graphene compound and an amphiphilic material may be conducted in the presence of a gas including at least one selected from the group consisting of an inert gas and carbon dioxide, or under the above gas atmosphere, and for example, it may be conducted under an atmosphere containing the above gas in the content of 50 vol % or more, 75 vol % or more, or 95 vol % or more in the air, or it may be conducted under an atmosphere substantially consisting only of the above gas.

Specifically, the sonication of an aqueous solution including a graphene compound and an amphiphilic material may be conducted in a state where the air contacting the surface of the aqueous solution mostly consists of a gas including at least one selected from the group consisting of an inert gas and carbon dioxide, and for example, 50 vol % or more, 80 vol % or more, or 95 vol % or more of the air contacting the surface of the aqueous solution may consist of at least one gas selected from the group consisting of the above inert gas and carbon dioxide.

Further, the sonication of an aqueous solution including a graphene compound and an amphiphilic material may be conducted in a closed type of reactor filled with a gas including at least one selected from the group consisting of an inert gas and carbon dioxide.

The closed type of reactor may be filled with a gas including at least one selected from the group consisting of an inert gas and carbon dioxide to 95 vol % or more, or the gas may be continuously injected into the closed type of reactor or circulated while being injected and discharged.

Meanwhile, the sonication may include applying sound waves of 5 to 20 kHz to the surface of the aqueous solution.

The method and apparatus that can be used in the step of applying sound waves of 5 to 20 kHz are not specifically limited, and for example, a common ultrasonic generator and the like may be used.

After the sonication of the aqueous solution including a graphene compound and an amphiphilic material is completed, formed organic microbubble complex particles may be sealed and kept in a container.

Meanwhile, the aqueous solution may include a graphene compound and an amphiphilic material.

The graphene compound may include graphene oxide, graphene, or a mixture thereof.

The graphene oxide and graphene are not specifically limited as long as they are prepared by a commonly known method, and the sizes and properties of graphene oxide and graphene that can be used in the preparation method of an organic microbubble complex particle according to one embodiment are not specifically limited.

The amphiphilic material refers to material having reactivity to both a water soluble material and an oil soluble material, and examples of the amphiphilic material that can be used may include a non-ionic surfactant and the like.

Specifically, as the amphiphilic material, a mixture of a compound having an HLB value of 10 or more and a compound having an HLB value of less than 10 may be preferably used.

The mixture of a compound having an HLB value of 10 or more and a compound having an HLB value of less than 10 may sufficiently secure reactivity to both a water soluble material and an oil soluble material, it may allow the graphene compound to be uniformly dispersed without agglomeration in the aqueous solution, and it may afford a uniform thickness and properties to the surface or shell layer of the organic microbubble complex particles prepared by the method according to one embodiment.

The mixing ratio of the compound having an HLB value of 10 or more and the compound having an HLB value of less than 10 is not specifically limited, and for example, the two kinds of compounds may be mixed in a weight ratio of 1:5 to 5:1.

Further, the amphiphilic material may include a mixture of a polyoxyethylene sorbitan fatty acid ester and a sorbitan fatty acid ester. Specific examples of the sorbitan fatty acid ester may include a SPAN surfactant and the like. Further, specific examples of the polyoxyethylene sorbitan fatty acid ester may include a TWEEN surfactant and the like.

The mixing ratio of the polyoxyethylene sorbitan fatty acid ester and the sorbitan fatty acid ester is not specifically limited, and the two kinds of compounds may be mixed at the weight ratio of 1:5 to 5:1.

Meanwhile, the aqueous solution may include 0.0001 to 1 parts by weight or 0.0005 to 0.1 parts by weight of the graphene compound, based on 100 parts by weight of the amphiphilic material.

If the content of the graphene compound is too low compared to the amphiphilic material in the aqueous solution, the external shape of the prepared organic microbubble complex particle may be nonuniform, or mechanical strength of the external surface may be low such that the gas in the organic microbubble complex particle may rapidly leak out, and when the organic microbubble complex particle is dried and then dispersed in a water soluble solvent, it may be difficult for the shape or property thereof to be recovered to the state before drying.

Further, if the content of the graphene compound is too high compared to the amphiphilic material in the aqueous solution, the external surface or shell layer of the organic microbubble complex particle may not form a firm structure, and thus gas in the organic microbubble complex particle may rapidly leak out and stability of the structure of the organic microbubble complex particle may be lowered.

Meanwhile, the preparation method of an organic microbubble complex particle according to one embodiment may further include a step of controlling pH of the aqueous solution to 0.5 to 7, or 1 to 5.

By controlling pH of the aqueous solution to 0.5 to 7, or 1 to 5, the external surface or shell layer of the prepared organic microbubble complex particle may have a firm structure.

In order to control pH of the aqueous solution, a common acid or alkali may be used.

According to yet another embodiment of the invention, a method for preparing an organic microbubble complex particle is provided, including injecting an aqueous solution including a graphene compound and an amphiphilic material, and a gas, into a microchannel.

The inventors confirmed through experiments that organic microbubble complex particles formed by injecting an aqueous solution including a graphene compound and an amphiphilic material, and a gas, into a microchannel may have high structural stability, may continue to exist for a long time in an aqueous solution, have little difference in particle size or particle diameter, and when used as an ultrasound contrast agent, have a high enhancement effect and excellent reproducibility of ultrasound contrast, and completed the invention.

By injecting the aqueous solution and gas into the microchannel, a longer time for reaction of the graphene compound and the amphiphilic material in the aqueous solution with gas may be secured, and thus the finally prepared organic microbubble complex particle may have a more stable 3-dimensional structure, and the reactivity between the gas, the graphene compound, and the amphiphilic material included in the organic microbubble complex particle may be further improved.

The organic microbubble complex particles prepared according to the method of the embodiment may continue to exist for a long time in an aqueous solution, and the size of formed particles may be uniform.

The organic microbubble complex particles of one embodiment include an organic microbubble complex particle group including two or more organic microbubble complex particles, as well as one organic microbubble complex particle.

The microchannel refers to a 3-dimensional structure including an empty space with an inner diameter of a microsize.

Specifically, the microchannel may have a length of 5 mm to 500 mm, and may have an inner diameter of 10 nm to 1000 μm, or 100 nm to 500 μm.

The prepared organic microbubble complex particle may have a maximum diameter of 1 μm to 500 μm, or 5 μm to 200 μm, and the maximum diameter may be distributed within the range of 50% to 150%, or 70% to 130%, compared to the mean of the maximum diameters.

Specifically, the maximum diameters of two or more organic microbubble complex particles included in the organic microbubble complex particle of one embodiment may have a value of 50% to 150%, or 70% to 130%, compared to the mean of the maximum diameters of the two or more organic microbubble complex particles.

As the aqueous solution including a graphene compound, an amphiphilic material, and a gas are injected into the microchannel and react, the organic microbubble complex particle may be prepared.

The prepared organic microbubble complex particle may include a core part including at least one gas selected from the group consisting of an inert gas and carbon dioxide, and a shell layer including a graphene compound and an amphiphilic material.

The shell layer may have a thickness of 0.01 μm to 100 μm, or 0.1 μm to 50 μm.

Further, the shell layer may be a porous layer including micropores having a maximum diameter of 0.001 μm to 1 μm.

The organic microbubble complex particle prepared by the above method, when redispersed in an aqueous solution after drying, may be immediately reconverted to a state before drying or to a bubble state due to the firm structure of the shell layer including a graphene compound and an amphiphilic material, and thus it may facilitate a commercial distribution process, and it may have various advantages in the application as a contrast agent.

Further, the prepared organic microbubble complex particle may be used as an ultrasound contrast agent due to the bubble property, and simultaneously, it may irradiate light after ultrasound diagnosis due to the photothermal effect of the graphene compound included in the shell layer and deliver drugs to a desired location, thus enabling a theragnosis (therapy+diagnosis) system capable of simultaneously conducting diagnosis and treatment.

The aqueous solution including a graphene compound and an amphiphilic material may be injected into the microchannel at a speed of 1 μl/h to 10,000 μl/h, 10 μl/h to 6000 μl/h, or 50 μl/h to 3000 μl/h.

In the preparation method of an organic microbubble complex particle, an inert gas such as helium, neon, argon, krypton, xenon, radon, nitrogen, and the like, carbon dioxide, or a mixture thereof may be used.

The gas may be injected into the microchannel at a speed of 1 μl/h to 10,000 μl/h, or 10 μl/h to 6000 μl/h, or 50 μl/h to 3000 μl/h.

If each injection speed of the aqueous solution including a graphene compound and an amphiphilic material and the gas is too low or too high, bubbles may not be produced, or the size of the produced bubbles may become nonuniform.

The ratio of the injection speed of the aqueous solution including a graphene compound and an amphiphilic material and the injection speed of the gas is not specifically limited, but for example, the ratio of the injection speed of the gas to the injection speed of the aqueous solution including a graphene compound and an amphiphilic material may be 0.005 to 500, or 0.01 to 100.

If the injection speed (injection pressure) of the gas is too much larger or too much smaller than the injection speed of the aqueous solution, a gas phase of a column shape may be generated in the channel, or adhesion between bubbles may be generated even if spherical bubbles are produced.

Further, if the injection speed of the aqueous solution is too much larger than the injection speed of the gas, bubbles may not be generated or small and unstable bubbles may be generated and disappear when passing through the channel.

The aqueous solution may include a graphene compound and an amphiphilic material.

The graphene compound may include graphene oxide, graphene, or a mixture thereof.

The graphene oxide and graphene are not specifically limited as long as they are prepared by a commonly known method, and the sizes and properties of the graphene oxide and graphene that can be used in the preparation method of an organic microbubble complex particle according to one embodiment are not specifically limited.

The amphiphilic material refers to a material having reactivity to both a water soluble material and oil soluble material, and examples of the amphiphilic material that can be used may include a non-ionic surfactant and the like. Specifically, as the amphiphilic material, a mixture of a compound having an HLB value of 10 or more and a compound having an HLB value of less than 10 may be preferably used.

The mixture of a compound having an HLB value of 10 or more and a compound having an HLB value of less than 10 may sufficiently secure reactivities to both a water soluble material and an oil soluble material, it may allow the graphene compound to be uniformly dispersed without agglomeration in the aqueous solution, and it may afford a uniform thickness and properties to the surface or shell layer of the organic microbubble complex particle prepared by the method according to one embodiment.

The mixing ratio of the compound having an HLB value of 10 or more and the compound having an HLB value of less than 10 is not specifically limited, and for example, the two kinds of compounds may be mixed in the weight ratio of 1:5 to 5:1.

Further, the amphiphilic material may include a mixture of a polyoxyethylene sorbitan fatty acid ester and a sorbitan fatty acid ester. Specific examples of the sorbitan fatty acid ester may include a SPAN surfactant and the like. Further, specific examples of the polyoxyethylene sorbitan fatty acid ester may include a TWEEN surfactant and the like.

The mixing ratio of the polyoxyethylene sorbitan fatty acid ester and the sorbitan fatty acid ester is not specifically limited, and the two kinds of compounds may be mixed at the weight ratio of 1:5 to 5:1.

Meanwhile, the aqueous solution may include 0.0001 to 1 parts by weight or 0.0005 to 0.1 parts by weight of the graphene compound, based in 100 parts by weight of the amphiphilic material.

If the content of the graphene compound is too low compared to the amphiphilic material in the aqueous solution, the external shape of the prepared organic microbubble complex particle may be nonuniform, or mechanical strength of the external surface may be low so gas in the organic microbubble complex particle may rapidly leak out, and when the organic microbubble complex particle is dried and then dispersed in a water soluble solvent, it may be difficult for the shape or property thereof to be recovered to the state before drying.

Further, if the content of the graphene compound is too high compared to the amphiphilic material in the aqueous solution, the external surface or shell layer of the organic microbubble complex particle may not form a firm structure, and thus gas in the organic microbubble complex particle may rapidly leak out, and stability of the structure of the organic microbubble complex particle may be lowered.

Meanwhile, the preparation method of an organic microbubble complex particle according to one embodiment may further include a step of controlling pH of the aqueous solution to 0.5 to 7, or 1 to 5.

By controlling pH of the aqueous solution to 0.5 to 7, or 1 to 5, the external surface or shell layer of the prepared organic microbubble complex particle may have a firm structure.

In order to control pH of the aqueous solution, a common acid or alkali may be used.

According to yet another embodiment of the invention, an organic microbubble complex particle is provided, including a core part including at least one gas selected from the group consisting of an inert gas and carbon dioxide, and a shell layer including a graphene compound and an amphiphilic material.

According to the preparation methods of the above-explained embodiments, an organic microbubble complex particle including a core part and a shell layer may be provided.

The details of the organic microbubble complex particle of the above embodiment are as explained in the preparation methods of the above explained embodiments.

The organic microbubble complex particles have high structural stability, may continue to exist for a long time in an aqueous solution, have little difference in particle size or particle diameter, and when used as an ultrasound contrast agent, may have a high enhancement effect or excellent reproducibility of ultrasound contrast.

As explained above, the organic microbubble complex particle, when redispersed in an aqueous solution after drying, may be immediately reconverted to a state before drying or to a bubble state due to the firm structure of the shell layer including a graphene compound and an amphiphilic material, and thus it may facilitate a commercial distribution process, and it may have various advantages in the application as a contrast agent.

Further, the organic microbubble complex particle may be used as an ultrasound contrast agent due to the bubble property, and simultaneously, it may irradiate light after ultrasound diagnosis due to the photothermal effect of the graphene compound included in the shell layer and deliver drugs to a desired location, thus enabling a theragnosis (therapy+diagnosis) system capable of simultaneously conducting diagnosis and treatment.

The organic microbubble complex particle may have a maximum diameter of 1 μm to 500 μm, or 5 μm to 200 μm, and the maximum diameter may be distributed within the range of 50% to 150%, or 70% to 130%, compared to the mean of the maximum diameters.

Specifically, the maximum diameters of two or more organic microbubble complex particles included in the organic microbubble complex particle of one embodiment may be a value of 50% to 150%, or 70% to 130% compared to the mean of the maximum diameters of the two or more organic microbubble complex particles.

The shell layer may have a thickness of 0.01 μm to 100 μm, or 0.1 μm to 50 μm.

Further, the shell layer may be a porous layer including micropores with a maximum diameter of 0.001 μm to 1 μm.

In the organic microbubble complex particle, at least one gas selected from the group consisting of an inert gas and carbon dioxide is located in a core part, and a shell layer including a graphene compound and an amphiphilic material may surround the core part.

Since the gas in the core part may directly contact the shell layer without a gap and exhibits high reactivity with the graphene compound and the amphiphilic material in the shell layer, the organic microbubble complex particle may have a more stable 3-dimensional structure, and it may continue to exist in an aqueous solution while maintaining a 3-dimensional structure for a long time.

Further, the organic microbubble complex particle may maintain the 3-dimensional structure including a shell layer and a core part even in a dried state, and even if it is redispersed in an aqueous solution and the like after drying, it may have a similar shape and properties to those before drying, and thus have high reproducibility. This is believed to result from the structural stability of the organic microbubble complex particle and high reactivity between constitutional elements.

Meanwhile, the organic microbubble complex particle may be contracted so as to have a maximum diameter of 1% to 25% compared to the initial maximum diameter in an aqueous solution. It is believed that this is because gas in the prepared organic microbubble complex particle is discharged outside in the form of ions, and thereby the graphene compound and the amphiphilic material constituting the shell layer of the organic microbubble complex particle closely bind with higher density.

Figure 7:
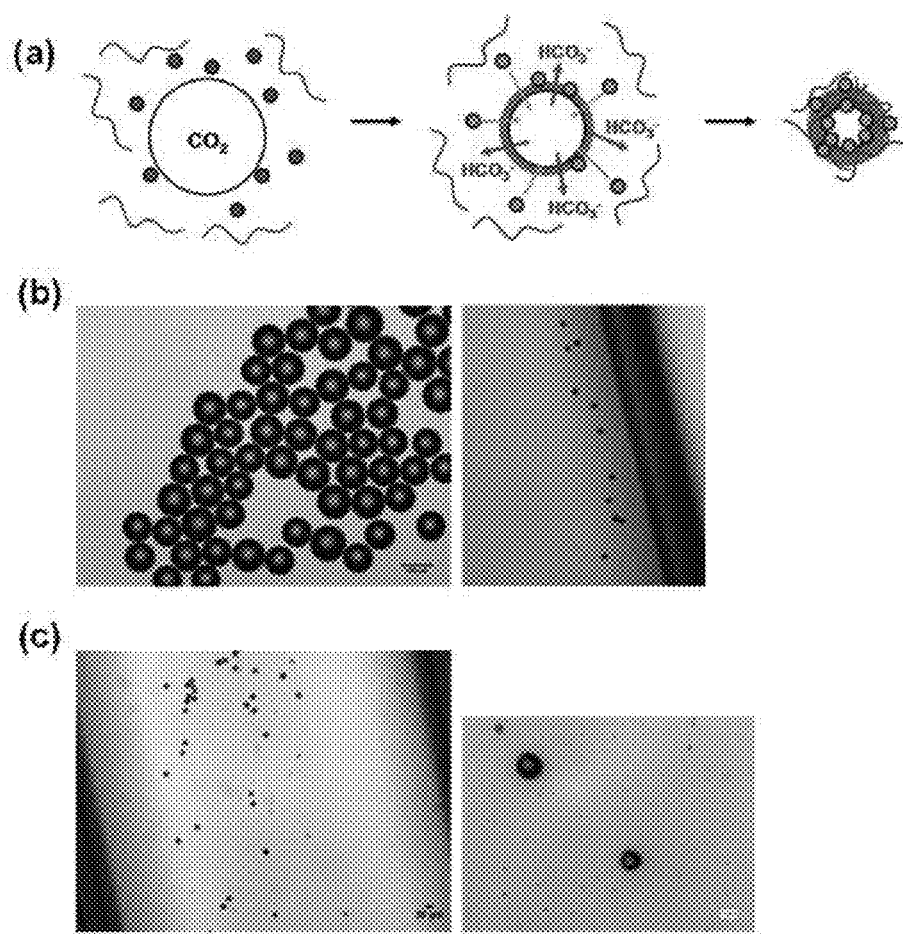
FIG. 7 shows (a) a schematic diagram showing a process of reduction of the size of the microbubble complex particles in Example 6, (b) optical microscopic photographs of the initial microbubble complex particles in a microchannel, and (c) optical microscopic photographs of the microbubble complex particles after about 5 hours had passed from the preparation.

For example, as shown in FIG. 7 (a), as carbon dioxide located in the organic microbubble complex particle (core) is discharged in the form of carbonate ions, and graphene oxide, sorbitan monostearate, and polyoxyethylene sorbitan monostearate constituting the shell layer closely bind with higher density, the organic microbubble complex particle may be contracted so as to have a maximum diameter of about 10% compared to the initial maximum diameter in the aqueous solution.

Meanwhile, the organic microbubble complex particle according to the above embodiment may continue to exist for about 3 hours or more, or 3 hours to 8 hours in the aqueous solution.

Specifically, the organic microbubble complex particle may continue to exist in an aqueous solution without change in the 3-dimensional structure and the like, and thus when used as an ultrasound contrast agent, it has a high enhancement effect and excellent reproducibility of ultrasound contrast, and simultaneously, it continues to exist in the body for a long time, thereby enabling contrast of the target part of the body.

According to yet another embodiment, an ultrasound contrast agent including the above-explained organic microbubble complex particles is provided.

As explained above, the microbubble complex particles have high structural stability, may continue to exist for a long time in an aqueous solution, and have little difference in particle size or particle diameter, and when used as an ultrasound contrast agent, may have a high enhancement effect and excellent reproducibility of ultrasound contrast.

The details of the ultrasound contrast agent are as explained in the preparation method and the organic microbubble complex particle of the above explained embodiments.

The ultrasound contrast agent may further include an aqueous solution in addition to the organic microbubble complex particles.

As the aqueous solution, those known to be usable as an ultrasound contrast may be used without specific limitations, and those having compatibility with the organic microbubble complex particle may be selected and used.

According to the present invention, organic microbubble complex particles that have high uniformity of particle size and excellent long term shape stability and storage stability, a method for preparing the organic microbubble complex particle, and a contrast agent that has a high enhancement effect, stability, and excellent reproducibility of ultrasound contrast may be provided.

The present invention will be explained in detail with reference to the following examples. However, these examples are only to illustrate the invention, and the scope of the invention is not limited thereto.

[Measurement Method]

1. In the following examples, comparative examples, and experimental examples, optical microscopic images of the prepared particles or bubbles were obtained using an upright microscope (Carl Zeiss Axio Plan II) equipped with a CCD camera (Qimaging Retiga 2000R Fast 1394), and the size of the particles or bubbles, size distribution, and stability were measured using the same.

2. Further, a particle tracking video was taken and recorded using an inverted microscope (Nikon Diaphot 300) and a high speed camera (Phantom V7.1), and scanning electron microscopy (SEM) was conducted at a range of 2.00 to 5.00 kV using an FEI Quanta 600 FEG ESEM apparatus.

COMPARATIVE EXAMPLE 1

Preparation of Organic Microbubble Complex Particles

As shown in FIG. 1 (a), a mixed solution (oil phase) of toluene and THF that included graphene oxide (GO), and nitrogen gas were injected into a microfluidic device that is filled with an aqueous solution (pH 2) including polyvinylalcohol (Mw, about 13,000 to 23,000) to prepare organic microbubble complex particles.

FIG. 1 (b) shows the optical microscopic photograph of the organic microbubble complex particles when the preparation was completed, and FIG. 1 (c) shows the optical microscopic photograph of the organic microbubble complex particles after 10 minutes had passed from the preparation.

As shown in FIGS. 1 (b) and (c), it was confirmed that if organic microbubble complex particles are prepared using a mixed solution obtained by adding 1 ml of an aqueous solution of graphene oxide (0.05 wt %) to 10 ml of a mixed solution of toluene and THF at a volume ratio of 1:1, organic microbubble complex particles including 1) an inner part including nitrogen gas, 2) a middle layer including graphene oxide (GO), toluene, and THF, and 3) an outer layer including polyvinylalcohol may be prepared, but the organic microbubble complex particles cannot continue to exist or maintain the shape for 10 minutes or more in an aqueous solution state.

COMPARATIVE EXAMPLE 2

Preparation of Organic Microbubble Complex Particles

As shown in FIG. 2 (a), while helium gas was injected into an aqueous solution of pH 5 that includes graphene oxide (GO), sonication was conducted at the interface of the aqueous solution and the air (using an ultrasonic generator Bandelin SONOPLUS HD200, 170 W output) to prepare organic microbubble complex particles, and the prepared organic microbubble complex particles were sealed and kept in a 2 ml container.

As shown in FIG. 2 (b), it was confirmed that the sizes of the prepared organic microbubble complex particles are nonuniform, and that the 3-dimensional structure is decomposed or disappears in the aqueous solution state within a short time after the preparation.

EXAMPLES 1 AND 2 AND COMPARATIVE EXAMPLE 3

Preparation of Organic Microbubble Complex Particles

EXAMPLE 1

The pH of a mixed solution of 1.73 mg/ml of sorbitan monostearate (Span 60), 8.27 mg/ml of polyoxyethylenesorbitan monooleate (Tween 80), and 0.01 mg/ml of graphene oxide (GO) was controlled to 2 using an 1 M HCl solution.

Further, helium gas was injected into the surface of the mixed solution to form a helium gas atmosphere, sonication was conducted at the surface of the mixed solution (using an ultrasound generator Bandelin SONOPLUS HD200, 170 W output) to prepare organic microbubble complex particles, and the prepared organic microbubble complex particles were sealed and kept in a 2 ml container.

As shown in FIG. 3 (a), it was confirmed that the prepared microbubble complex particles have uniform particle diameters (24.54±4.85 µm), and that they have an uneven spherical surface with eccentricity of 0.887 as measured by the Image J program.

Further, as shown in FIG. 3 (b), it was confirmed that even after 3 days had passed from the time of preparation, the microbubble complex particles maintain similar shape and size to those at the beginning.

It is believed that the microbubble complex particles may stably maintain the shape and the like for a long time because a shell layer including sorbitan monostearate polyoxyethylenesorbitan monostearate and graphene oxide is formed in a thick and stable structure, and a core part including a gas is formed inside of the shell layer. Further, since the shell layer may have high reactivity with gas in the core part while having a stable structure, diffusion of the gas outside of the microbubble complex particles may be minimized.

EXAMPLE 2

Organic microbubble complex particles were prepared by the same method as Example 1, except that after preparing a mixed solution of 1.73 mg/ml of sorbitan monostearate (Span 60), 8.27 mg/ml of polyoxyethylenesorbitan monooleate (Tween 80), and 0.01 mg/ml of graphene oxide (GO), pH of the mixed solution was not controlled. Further, the prepared organic microbubble complex particles were sealed and kept in a 2 ml container.

The prepared organic microbubble complex particles have an average particle diameter of 24.54±4.85 µm, and show an uneven spherical surface after 3 days passed from the time of preparation, and thus it was confirmed that shape stability is maintained for a long time.

COMPARATIVE EXAMPLE 3

Organic microbubble complex particles were prepared by the same method as Example 1, except that a mixed solution of 1.73 mg/ml of sorbitan monostearate (Span 60) and 8.27 mg/ml of polyoxyethylenesorbitan monooleate (Tween 80) (without graphene oxide) was used, and the pH of the mixed solution was not controlled. Further, the prepared organic microbubble complex particles were sealed and kept in a 2 ml container.

The prepared organic microbubble complex particles have diameters of 10 µm to 100 µm, and it was confirmed that the small bubble complex particles are dissolved in an aqueous solution and disappear within a short time.

EXAMPLES 3 TO 4 AND COMPARATIVE EXAMPLE 4

Preparation of Organic Microbubble Complex Particles Using Microchannel

EXAMPLE 3

(1) Preparation of Organic Microbubble Complex Particles Using a Microchannel

A mixed solution of 1.73 mg/ml of sorbitan monostearate (Span 60), 8.27 mg/ml of polyoxyethylenesorbitan monooleate (Tween 80), and 0.01 mg/ml of graphene oxide (GO) was prepared, and the pH of the mixed solution was controlled to 2 using an 1 M HCl solution.

The mixed solution of which pH was controlled to 2 and nitrogen gas were simultaneously injected into a microchannel having a length of 260 mm and an inner diameter of about 12 µm using a syringe pump (Harvard Apparatus, PHD 2000 series) to prepare organic microbubble complex particles, and the prepared organic microbubble complex particles were sealed and kept in a 2 ml container.

At this time, the mixed solution was injected into the microchannel at a speed of about 1000 µl/h, and the nitrogen gas was injected into the microchannel at a speed of about 100 µl/h.

Figure 4:
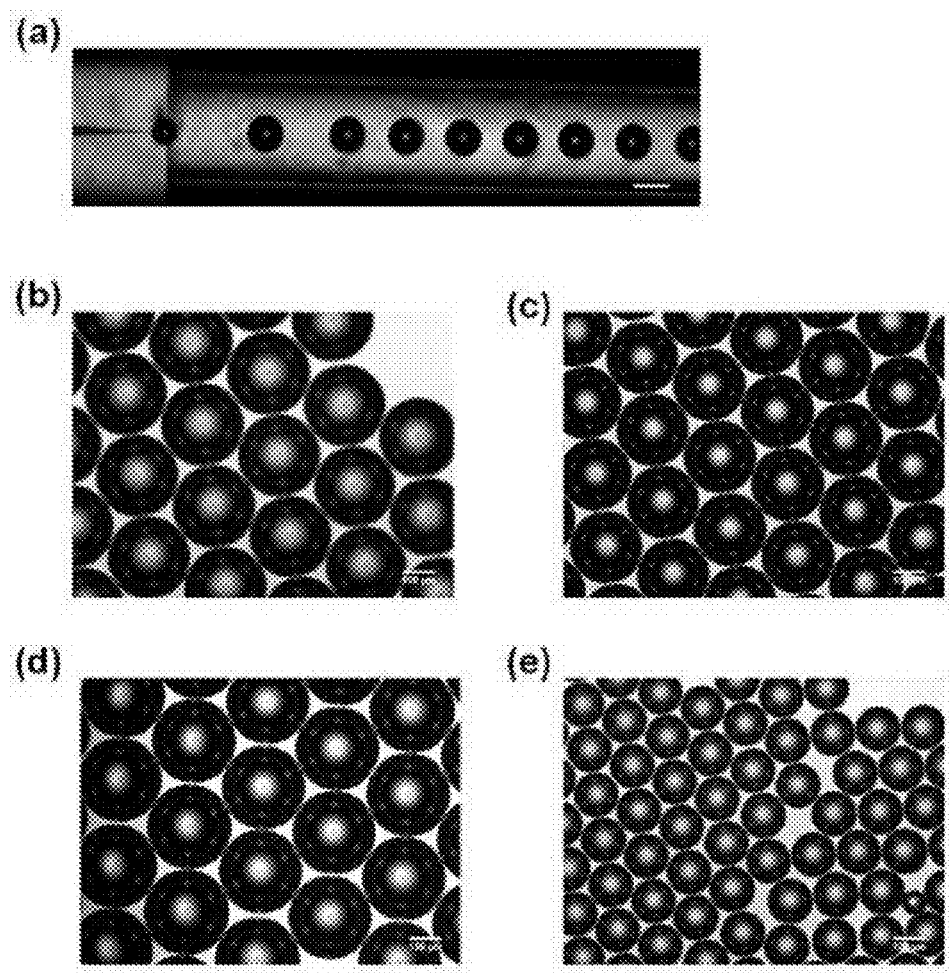
FIG. 4 shows (a) one example of the preparation method of the organic microbubble complex particles using a microchannel that is used in Examples 3 and 4 and Comparative Example 4, (b) an optical microscopic photograph of the organic microbubble complex particles obtained in Comparative Example 4, (c) an optical microscopic photograph of the organic microbubble complex particles obtained in Example 5, (d) an optical microscopic photograph of the organic microbubble complex particles obtained in Example 3, and (e) an optical microscopic photograph of the organic microbubble complex particles obtained in Example 4.

The optical microscopic photograph of the microbubble complex particles obtained in Example 3 is shown in FIG. 4 (d).

(2) Drying of the Prepared Organic Microbubble Complex Particles

The prepared organic microbubble complex particles were naturally dried at room temperature.

Figure 5:
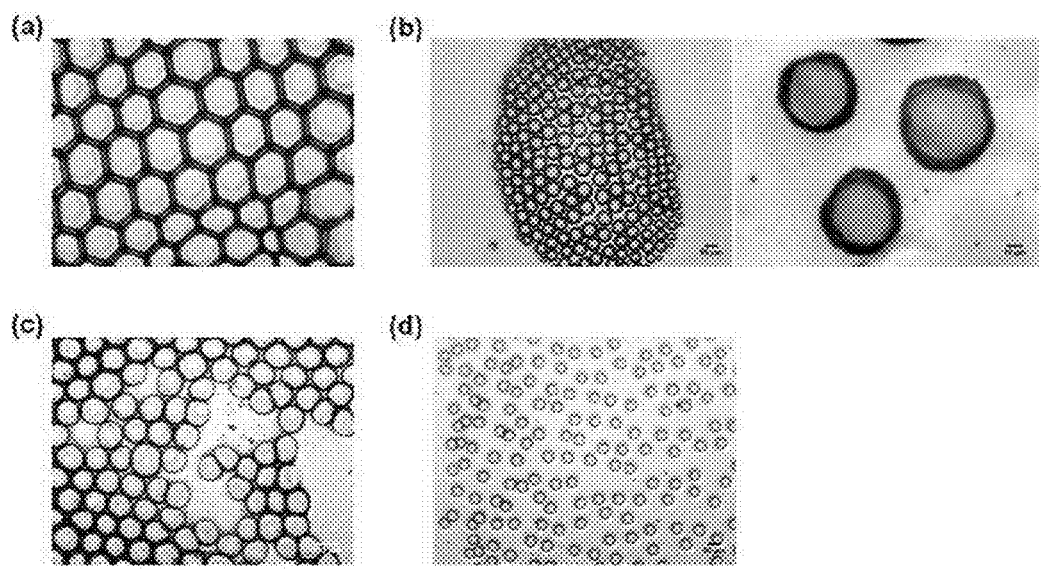
FIG. 5 shows (a) an optical microscopic photograph of the dried organic microbubble complex particles obtained in Comparative Example 4, (b) optical microscopic photographs of the dried organic microbubble complex particles obtained in Example 5, (c) an optical microscopic photograph of the dried organic microbubble complex particles obtained in Example 3, and (d) an optical microscopic photograph of the dried organic microbubble complex particles obtained in Example 4.

The optical microscopic photograph of the dried microbubble complex particles is shown in FIG. 5 (c).

As shown in FIG. 5 (c), it was confirmed that the microbubble complex particles obtained in Example 3 maintain the spherical or circular 3-dimensional structure even in the dried state.

(3) Redispersion of Dried Organic Microbubble Complex Particle in Aqueous Solution Five hours after the drying was completed, the dried organic microbubble complex particles were redispersed in distilled water.

Figure 6:
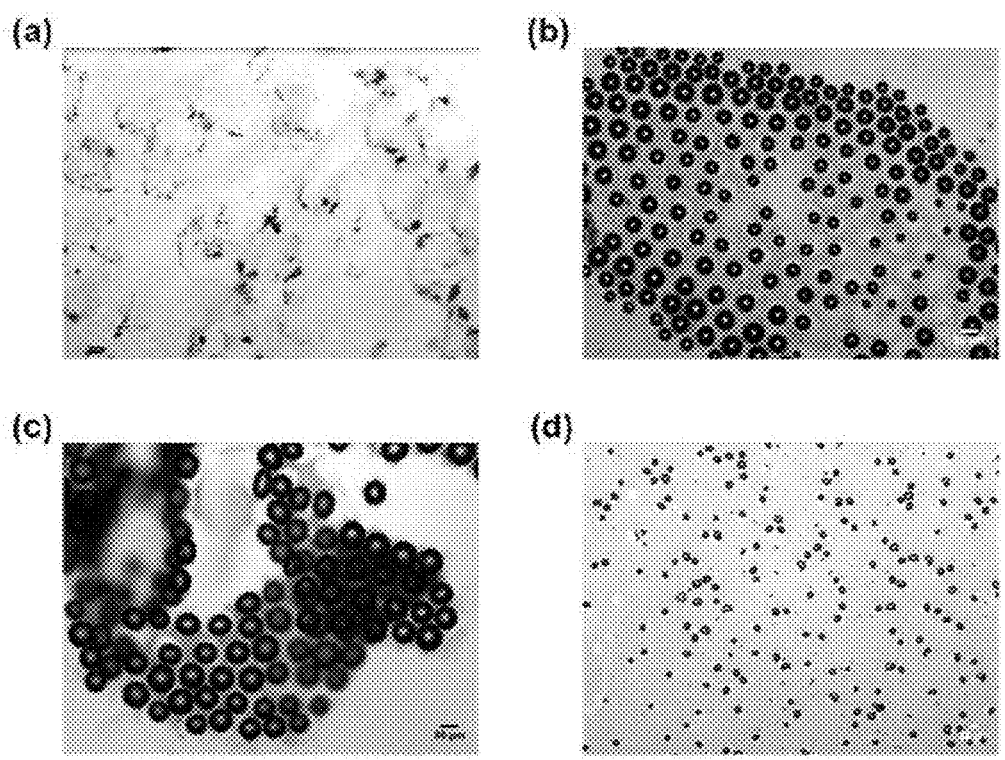
FIG. 6 shows (a) an optical microscopic photograph of the organic microbubble complex particles that are dried and then redispersed in an aqueous solution in Comparative Example 4, (b) an optical microscopic photograph of the organic microbubble complex particles that are dried and then redispersed in an aqueous solution in Example 5, (c) an optical microscopic photograph of the organic microbubble complex particles that are dried and then redispersed in an aqueous solution in Example 3, and (d) an optical microscopic photograph of the organic microbubble complex particles that are dried and then redispersed in an aqueous solution in Example 4.

The optical microscopic photograph of the redispersed microbubble complex particles is shown in FIG. 6 (c).

As shown in FIG. 6 (c), it was confirmed that even if the microbubble complex particles obtained in Example 3 are dried and then redispersed in an aqueous solution, they have a similar shape and properties to those before drying.

EXAMPLE 4

(1) Preparation of Organic Microbubble Complex Particles Using Microchannel

Organic microbubble complex particles were prepared by the same method as Example 3, except that the mixed solution of which pH was controlled to 2 was injected into the microchannel at a speed of about 100 µl/h, and the nitrogen gas was injected into the microchannel at a speed of about 3000 µl/h.

The optical microscopic photograph of the microbubble complex particles obtained in Example 4 is shown in FIG. 4 (e).

(2) Drying of the Prepared Organic Microbubble Complex Particles

The prepared organic microbubble complex particles were dried by the same method as Example 3.

The optical microscopic photograph of the dried microbubble complex particles is shown in FIG. 5 (d).

As shown in FIG. 5 (d), it was confirmed that the microbubble complex particles obtained in Example 4 maintain the spherical or circular 3-dimensional structure even in the dried state.

(3) Redispersion of Dried Organic Microbubble Complex Particle in Aqueous Solution Five hours after the drying was completed, the dried organic microbubble complex particles were redispersed in distilled water.

The optical microscopic photograph of the redispersed microbubble complex particles is shown in FIG. 6 (d).

As shown in FIG. 6 (d), it was confirmed that even if the microbubble complex particles obtained in Example 4 are dried and then redispersed in an aqueous solution, they have a similar shape and properties to those before drying.

EXAMPLE 5

(1) Preparation of Organic Microbubble Complex Particles Using a Microchannel

Organic microbubble complex particles were prepared by the same method as Example 3, except that the pH of the mixed solution was not controlled after the mixed solution was prepared.

The optical microscopic photograph of the microbubble complex particles obtained in Example 5 is shown in FIG. 4 (c).

(2) Drying of the Prepared Organic Microbubble Complex Particles

The prepared organic microbubble complex particles were dried by the same method as Example 3.

The optical microscopic photograph of the dried microbubble complex particles is shown in FIG. 5 (b).

As shown in FIG. 5 (b), it was confirmed that the microbubble complex particles obtained in Example 5 maintain the spherical or circular 3-dimensional structure even in the dried state.

(3) Redispersion of Dried Organic Microbubble Complex Particle in Aqueous Solution 5 hours after the drying was completed, the dried organic microbubble complex particles were redispersed in distilled water.

The optical microscopic photograph of the redispersed microbubble complex particles is shown in FIG. 6 (b).

As shown in FIG. 6 (b), it was confirmed that even if the microbubble complex particles obtained in Example 5 are dried and then redispersed in an aqueous solution, they have a similar shape and properties to those before drying.

COMPARATIVE EXAMPLE 4

(1) Preparation of Organic Microbubble Complex Particles Using a Microchannel

Organic microbubble complex particles were prepared by the same method as Example 3, except that a mixed solution of 1.73 mg/ml of sorbitan monostearate (Span 60) and 8.27 mg/ml of polyoxyethylenesorbitan monooleate (Tween 80) (without graphene oxide) was used, and pH of the mixed solution was not controlled.

The optical microscopic photograph of the microbubble complex particles obtained in Comparative Example 4 is shown in FIG. 4 (b).

(2) Drying of the Prepared Organic Microbubble Complex Particles

The prepared organic microbubble complex particles were dried by the same method as Example 3.

The optical microscopic photograph of the dried microbubble complex particles is shown in FIG. 5 (a).

As shown in FIG. 5 (a), it was confirmed that the microbubble complex particles obtained in Comparative Example 4, if dried, cannot maintain the 3-dimensional structure and cannot exist as circular or spherical particles.

(3) Redispersion of Dried Organic Microbubble Complex Particles in Aqueous Solution Five hours after the drying was completed, the dried organic microbubble complex particles were redispersed in distilled water.

The optical microscopic photograph of the microbubble complex particles that are dried and then redispersed is shown in FIG. 6 (a).

As shown in FIG. 6 (a), the dried microbubble complex particles obtained in Comparative Example 4 are mostly dissolved as they are redispersed in distilled water, and thus, the 3-dimensional structure of the particles could not be observed.

EXAMPLE 6

Drying of Organic Microbubble Complex Particles Prepared Using Microchannel and Redispersion with a Solvent (1) Preparation of Organic Microbubble Complex Particles Using a Microchannel Organic microbubble complex particles were prepared by the same method as Example 3, except that instead of nitrogen gas, a mixture of carbon dioxide and helium (0.5 vol %) was injected through a gas injector at a speed of 100 µl/h, and the prepared organic microbubble complex particles were sealed and kept in a 2 ml container.

As shown in FIG. 7 (b), the maximum diameter of the microbubble complex particles that are initially produced in a microchannel is about 100 µm, but when the prepared organic microbubble complex particles are sealed and kept in the container for about 5 hours, the maximum diameter decreased to about 10 µm [FIG. 7 (c)].

It is believed that this is because carbon dioxide in the organic microbubble complex particles (core) is discharged outside in the form of carbonate ions, and thereby graphene oxide, sorbitan monostearate, and polyoxyethylene sorbitan monostearate forming the shell layer of the organic microbubble complex particle more closely bind with higher density.

The schematic diagram of this process is as shown in FIG. 7 (a).

What is claimed is:

1. A method for preparing organic microbubble complex particles, comprising injecting an aqueous solution comprising a graphene compound and an amphiphilic material, and a gas, into a microchannel,
    wherein the amphiphilic material includes a mixture of polyoxyethylene sorbitan fatty acid ester and sorbitan fatty acid ester mixed at a weight ratio of 1:5 to 5:1, and
    wherein the aqueous solution includes the graphene compound in a content of 0.001 to 0.1 parts by weight, based on 100 parts by weight of the amphiphilic material.

2. The method for preparing organic microbubble complex particles according to claim 1,
    wherein the microchannel has a length of 5 mm to 500 mm and an inner diameter of 10 nm to 1000 µm.

3. The method for preparing organic microbubble complex particles according to claim 1,
    wherein the aqueous solution comprising a graphene compound and an amphiphilic material is injected into the microchannel at a speed of 1 µl/h to 10,000 µl/h.

4. The method for preparing organic microbubble complex particles according to claim 1,
    wherein the gas is injected into the microchannel at a speed of 1 µl/h to 10,000 µl/h.

5. The method for preparing organic microbubble complex particles according to claim 1,
    wherein the gas includes at least one selected from the group consisting of an inert gas and carbon dioxide.

6. The method for preparing organic microbubble complex particles according to claim 1,
    wherein the graphene compound includes at least one selected from the group consisting of graphene oxide and graphene.

7. The method for preparing organic microbubble complex particles according to claim 1,
    further comprising a step of controlling the pH of the aqueous solution to 0.5 to 7.

\* \* \* \* \*